United States Patent
Kállay et al.

[11] Patent Number: 5,247,102
[45] Date of Patent: Sep. 21, 1993

[54] PROCESS FOR THE PREPARATION OF SUBSTITUTED ISOFLAVONE DERIVATIVE

[75] Inventors: Tamás Kállay; György Lányi; László Ledniczky; Lajos Imrei; György Hoffmann; Mária Sziládi; Éva Somfai; Tibor Montay, all of Budapest, Hungary

[73] Assignee: Chinoin Gyogyszer- es Vegyeszeti Termekek Gyara Rt., Budapest, Hungary

[21] Appl. No.: 778,927

[22] PCT Filed: Apr. 6, 1990

[86] PCT No.: PCT/HU90/00023
§ 371 Date: Dec. 5, 1991
§ 102(e) Date: Dec. 5, 1991

[87] PCT Pub. No.: WO91/15483
PCT Pub. Date: Oct. 17, 1991

[51] Int. Cl.$^5$ .............................................. C07D 311/36
[52] U.S. Cl. .................................................... 549/403
[58] Field of Search ......................................... 549/403

[56] References Cited

U.S. PATENT DOCUMENTS 4,644,012 2/1987 Tsuda et al. ........................ 514/456

Primary Examiner—Nicky Chan
Attorney, Agent, or Firm—Herbert Dubno; Jonathan Myers

[57] ABSTRACT

The invention relates to a process for the preparation of pure isoflavone derivatives of the general formula (I),

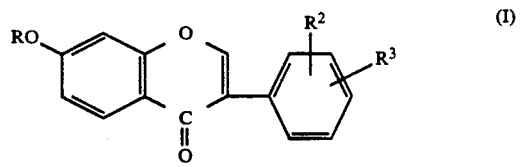

wherein
R stands for hydrogen or isopropyl,
$R^2$ and $R^3$ stand for hydrogen or $C_{1-2}$ alkoxy by reacting a rezorcinol-derivative of the general formula (III)

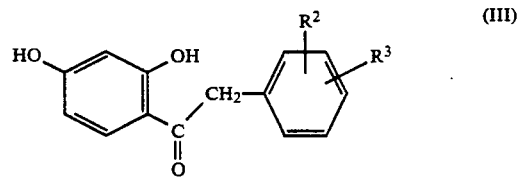

wherein $R^2$ and $R^3$ are as given above with ethyl-orthoformiate of the formula (IV)

$$(C_2H_5O)_3 CH \qquad (IV)$$

in the presence of a base and optionally by alkylating the product.

22 Claims, No Drawings

PROCESS FOR THE PREPARATION OF SUBSTITUTED ISOFLAVONE DERIVATIVE

Cross Reference to Related Application

This application is a National Phase of PCT/HU90/00023 filed Apr. 6, 1990.

FIELD OF THE INVENTION

The present invention relates to an improved process for the preparation of substituted isoflavone derivatives of high purity, which are suitable for the preparation of pharmaceutical compositions, particularly for the preparation of ipriflavon (Osteochin[R]) which is the common name of 7-isopropoxy-isoflavone suitable for use against osteoporosis (HU-PS 162 377).

In the specification the substituents are defined as follows:

R stands for hydrogen or isopropyl;
$R^2$ and $R^3$ stand for hydrogen or $C_{1-2}$alkoxy.

According to the invention pure isoflavone derivatives of the formula (I)

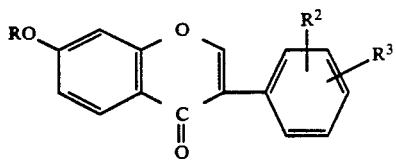

can be prepared by reacting resorcinol-derivatives of the formula (III)

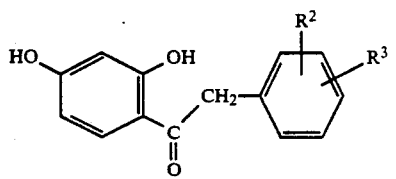

and ethyl-ortho-formate

 (IV)

in the presence of a base and optionally by alkylating the products whereby the compounds of the formula (III) and (IV) are subjected to ring closure in the presence of an organic solvent, preferably dimethylformamide and/or isopropanol and/or in a 0.3-2-fold volume calculated to the volume of the resorcinol derivatives of the formula (III) and/or in the presence of excess ester of the formula (IV) at a temperature of 70°-100° C., whereupon the reaction mixture becomes supersaturated (20-70% by weight) related to the product of the formula (VII)

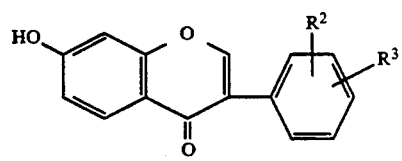

and thus the product of the formula (VII) continuously precipitates from the reaction mixture in the course of the reaction. After cooling the reaction mixture the product of the formula (VII) is filtered without or with the addition of a solvent or an almost equivalent amount of anhydrous potassium carbonate is added and the crystallizing double salt of the formula (V)

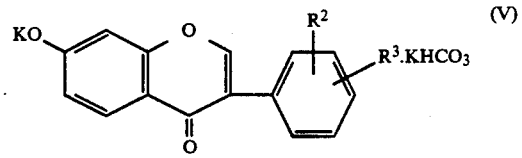

is isolated while the contaminant of the formula (VI)

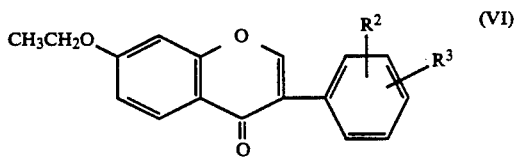

remains in the solution, or dissolves selectively, whereafter the product of the formula (V) or (VII) is reacted with isopropyl halide and the pure product containing up to 0.5% by weight of the contaminant of the formula (VI) is optionally separated.

BACKGROUND OF THE INVENTION

As is known, the appropriately substituted 7-hydroxy-isoflavone-derivatives are suitable intermediates in the synthesis of 7-alkoxy-isoflavones which are effective medicines in human and veterinary therapy. Thus, it is desirable to prepare the 7-hydroxy-isoflavone-derivative of the formula (VII) in such chemical purity that it should be suitable for the preparation of the 7-alkylated end-product in appropriate purity, that is, it is an important requirement to suppress the formation of the contaminating derivatives of the formula (VI).

The 7-hydroxy-derivative of the formula (VII) can be prepared in the industry by subjecting the resorcinol-derivative of the formula (III) and an orthoformic acid ester of the general formula (IV) to ring closure. The following methods are known for carrying out the above synthesis:

In a pyridine-piperidine mixture by boiling for 1 hour (CA. 56, 2408) with a yield of 80% with 70% perchloric acid or $POCl_3$-dimethyl-formamide (Zsurn. Chem. Khim. 1970 40/2459; CA 75. 201219), with a yield of 33% using HCl as a catalyst (CA. 83, 193010), with a yield of 70%. In an analogous process the mixture is boiled for 8 hours in pyridine/piperidine mixture and unsubstituted isoflavone is prepared with a yield of 60% starting from 2-hydroxy-phenyl-benzyl-ketone (US-PS 3 340 276).

The mentioned ring closures are all performed at 110°-150° C. in the presence of a mixture of a solvent boiling at a temperature above 100° C. (pyridine homologs, dimethyl-formamide etc ) and a secondary amine (piperidine, morpholine, pyrrolidine) preferably at the boiling point of &he mixture. In some cases the formed alcohol is distilled off during reaction, presumably in order to improve conversion or in order to raise temperature.

When reproducing said processes we have found that in addition to 7 hydroxy-isoflavone derivatives of the formula (VII) a significant amount& (in some cases 2–10% by weight measured by HPLC) of 7-ethoxy-isoflavone-derivative of the formula (VI) is formed among to other side products. By reducing the molar excess of ethyl-orthoformiate the yield is significantly reduced but the 7-ethoxy-isoflavone contamination cannot be eliminated. The 7-hydroxy-isoflavone-derivative of the formula (VII) prepared by this method can be purified only by an expensive me&hod using several solvent treatments.

DESCRIPTION OF THE INVENTION

We have found that unlike the reaction disclosed in the literature a moderate ring closure can he used so that the formed 7-hydroxy-isoflavone of the formula (VII) starts to crystallize from the reaction mixture shortly after the reaction is initiated.

The pure 7-hydroxy-isoflavone derivatives of the formula (VII) isolated from the reaction mixture contain such a small amount of contaminant of formula (VI) (about 0.1–0.5% by weight measured by HPLC) and other side-products that they can be eliminated if desired by one single purification step.

We have further found that the contaminant of the formula (VI) can be removed from the product by isolating a novel potassium-double salt.

When performing the ring closing reaction one may preferably proceed by performing the reaction at 80°–90° C. and using a heat treatment for 6–10 hours. It is further preferred to promote the supersaturation by retaining ethanol formed in the reaction during the ring closure. It is further preferred &o use a base catalyst for the ring closure, such as a secondary amine, preferably morpholine, piperidine or pyrrolidine.

During ring closure we found it to be most preferable to react a ketone of the formula (III) with 20% by mole excess of orthoformic acid ester and a 0.3–2-fold amount of solvent and about 20% by mole of a secondary amine at 80°–90° C. After about 30–60 minutes 7-hydroxy-isoflavone of the formula (VII) starts to crystallize from the reaction mixture. The reaction is continued until the complete conversion of the starting ketone of the formula (III). Yield is above 90%, and the obtained product contains a contamination of the formula (VI) in less than 0.1–0.5% by weight shown by HPLC method.

The double salt of the formula (V) is formed from the reaction mixture by using an apolar solvent, preferably toluene with an anhydrous potassium carbonate at 40°–80° C., preferably at 60° C. By isolating a double salt a further purification and separation, respectively, is conducted. The double salt can be directly alkylated with alkyl-halide, without an acid-binding agent in a suitable solvent, such as dimethyl formamide or ketone. Thus, 7-isopropoxy-isoflavone derivatives can be obtained in a pure state.

The final step of the process according to the invention is the optional alkylation of the pure 7-hydroxy-isoflavone. The alkylation can preferably be carried out in the presence of a potassium carbonate acid-binding agent in acetone or dimethyl-formamide medium with alkyl-bromide. Under suitable conditions the product obtained after ring-closure contains less than 0.1% by weight of 7-ethoxy-isoflavone and this product can be used for preparing pharmaceutical compositions.

Further advantages of the process according to the invention are:
that the process ensures a yield higher than 10% related to the method used in the literature;
a particularly pure chemical can be obtained, which is of pharmaceutical quality.

SPECIFIC EXAMPLES

The further details of the invention are illustrated by the following examples.

Example 1

62.5 g (0.274 mole) of 2,4-dihydroxy-phenyl-benzyl-ketone, 105 ml of isopropanol, 5 ml of morpholine and 49.7 g (0.33 mole) ethyl-orthoformate are stirred for 7 hours at 80°–90° C. During the reaction in the first half hour the crystals start to precipitate. At the end of the reaction the crystalline suspension is cooled to −5° C. and filtered. After drying 59.1 g of 7-hydroxy-isoflavone are obtained.

Yield: 90.6%.

The active ingredient content of the product is above 98% by spectroscopy.

7-ethoxy-isoflavone contamination by HPLC method: 0.2–0.4% by weight.

Example 2

We proceed as disclosed in example 1. When the reaction is completed 50 ml of solvent are distilled off from the crystalline suspension and 160 ml of methanol are added under stirring. The mixture is stirred at 58°–60°0 C. for 20 minutes, whereafter it is crystallized at −5° C. The precipitated substance is filtered and dried. 58.8 g of 7-hydroxy-isoflavone are obtained.

Yield: 90.1%. Active-ingredient content is above 98% (by spectroscopy).

Contamination of 7-ethoxy-isoflavone by HPLC method: 0.2–0.3% by weight.

Example 3

90 ml of solvent are distilled off the reaction mixture as obtained in Example 1, whereafter 37.8 g (0.274 mole) of anhydrous potassium-carbonate and 200 ml of toluene are added, and the reaction mixture is stirred for 30 minutes at 60°–65° C. followed by stirring at 0°–(−5)° C. for 2 hours. The double salt containing 7-hydroxy-isoflavone-potassium salt and potassium-hydrogen-carbonate is filtered and dried. 98.5 g of a double salt is obtained.

Yield: 95%.

| Analysis: $C_{15}H_9O_3K \cdot KHCO_3$ | Molecular weight: 376 | |
|---|---|---|
| | Calculated | Found |
| C % | 51.06 | 51.9 |
| H % | 2.66 | 2.76 |
| K % | 20.7 | 21.8 |

NMR by BRUKER WP-80 spectrophotometer im DMSO-$d_6$ solvent by using a TMS inert standard

| $^1H$ | "double salt" | 7-hydroxy-isoflavone |
|---|---|---|
| 5 C—H | 7.50 ppm (d) $^3J = 9$ Hz | 8.00 ppm (d) $^3J = 9$ Hz |
| 6 C—H | 6.13 ppm (dd) | 6.90 ppm (dd) |
| 8 C—H | 5.77 ppm (d) $^4J = 2$ Hz | 6.87 ppm (d) $^4J = 2$ Hz |
| $^{13}C$ | | |
| 7 C | 174.93 ppm | 156.82 ppm |

The obtained double-salt is dissolved in a three-fold amount of methanol and water at 50°–60° C. The solution is clarified and filtered. The pH value of the filtrate is adjusted to 1 by using an 1:1 dilution of aqueous hydrochloric-acid, the precipitated material is filtered, washed to neutral and dried. 58.7 g of 7-hydroxy-isoflavone are obtained. The product contains 98% by weight of pure product by spectroscopy.

7-ethoxy-isoflavone content by HPLC method: 0.1% by weight.

Yield: 90%.

Example 4

50 g (0.219 mole) of a mixture of 2,4-dihydroxy-phenyl-benzyl-ketone, 20 ml of dimethyl-formamide, 2.6 ml of morpholine and 39.06 g (0.26 mole) of ethyl-orthoformate is stirred for 7 hours at 80°-90° C. After 25 minutes crystallization can be observed. At the end of the reaction time the crystallized suspension is diluted with 120 ml of chloroform and it is crystallized at 0° C. for 2 hours. After filtration the product is covered twice with 45 ml of chloroform and dried. 47.9 g of 7-hydroxy-isoflavone are obtained.

Yield: 91.9%.

7-ethoxy-isoflavone contamination by HPLC method: 0.1–0.3% by weight.

Example 5

25 g (0.1096 mole) of a mixture of 2,4-dihydroxy-phenyl-benzyl-ketone, 12.5 ml dimethyl-formamide, 2 ml of piperidine and 19.7 g (0.133 mole) of ethylorthoformiate is stirred for 16 hours at 80°-90° C. and diluted with 65 ml of chloroform. The precipitated substance is isolated and boiled with an 8:1 mixture of chloroform:methanol and it is filtered and dried. 23.5 g 7-hydroxy-isoflavone are obtained.

Yield: 90%.

Product-content by spectroscopy: 98.5% by weight.

7-ethoxy-isoflavone content: 0.2–0.4% by weight (HPLC).

Example 6

A mixture of 20 g (0.0877 mole) 2,4-dihydroxy-phenyl-benzyl-ketone, 20.7 g (0.14 mole) ethyl-orthoformate and 1 ml of morpholine is stirred on a hot water bath. Crystallization starts after heating for 25 minutes. The inert temperature falls back to 87° C. from 96° C. during the reaction. After stirring for 5 hours the reaction mixture is diluted with 48 ml of chloroform and then one may proceed as disclosed in Example 5. 18.9 g of 7-hydroxy-isoflavone are obtained.

Yield: 90.6%. Content by spectroscopy: 99% by weight, 7-ethoxy-isoflavone content: 0.1–0.2% by weight (HPLC).

Example 7

A mixture of 100 kg (438.5 mole) of 2,4-dihydroxy-phenyl-benzyl-ketone, 38 kg of dimethyl-formamide, 5.2 kg of morpholine and 75 kg (506 mole) of ethyl-orthoformate is stirred at 80°-90° C., while within one hour crystallization is initiated. 360 kg of chloroform are added to the suspension after 7 hours at 60° C. After cooling the crystalline substance is centrifuged, covered with chloroform, filtered and dried. 94.5 kg of 7-hydroxy-isoflavone are obtained, 7-ethoxy-isoflavone content: 0.1% by weight, yield: 90.5%.

Example 8

98.5 g of double salt are suspended in 100 ml of dimethyl-formamide. 44 g (0.36 mole) isopropyl-bromide are added, and the reaction mixture is stirred at 75°-80° C. for 2 hours and then poured on 250 ml of water. The precipitated substance is filtered, washed with water to neutral and dried at 60° C. 66 g of 7-isopropoxy-isoflavone are obtained, active ingredient content: 99.5%, drying loss is 0.1%, 7-ethoxy-isoflavone-content: 0.1%. Yield: 86.1%, calculated to 2,4-dihydroxy-phenyl-benzyl-ketone.

Example 9

14.4 g (0.05 mole) of 2,4-dihydroxy-phenyl-(3',4'-dimethoxy-benzyl)-ketone are reacted with 10.5 g (0.07 mole) ethyl-orthoformate in 10 ml of dimethyl-formamide in the presence of 1 ml morpholine. The reaction mixture is maintained at 80°-85° C., and in the second hour a solid precipitates. After 6 hours 100 ml of chloroform are added to the mixture, the precipitated substance is filtered and dried. 7-hydroxy-3',4'-dimethoxy-isoflavone is obtained.

Mp.: 259°–262° C.

After recrystallization from dimethyl-formamide the product melts at 263°–264° C.

| Analyses: | $C_{17}H_{14}O_5$ | Molecular weight: 298 |
|---|---|---|
| calculated: | C % = 68.46% | H % = 4.69%; |
| found: | C % = 68.30% | H % = 4.72%. |

The product is identical according to NMR test.

Thin layer chromatography:

developing system: toluene:n-butyl-acetate-acetic-acid = 8:2:1

Adsorbent: Kieselgel 60 $F_{254}$ (Merck)

Application: 0.2 g (10 ml dimethyl-formamide 100 /ug)

Front: 16 cm

Development: in UV light az 254 nm

Rf = 0.4.

Example 10

47.4 g (0.15 mole) 2,4-dihydroxy-phenyl-3,4-ethoxy-benzyl-ketone are reacted with 31.5% (0.21 mole) ethyl-orthoformate in 20 ml of dimethyl-formamide in the presence of 3 ml morpholine. The reaction mixture is maintained at 80°-85° C. for six hours. Upon cooling to 60° C. 100 ml of chloroform are added. The precipitated substance is filtered and dried. Product: 7-hydroxy-3',4'-diethoxy-isoflavone.

M.p.: 189°–191° C.

After recrystallization from dimethyl-formamide: m.p.: 192°–193° C.

Analysis for the formula $C_{19}H_{18}O_5$:

calculated: C % = 69.93; H % = 5.52;

found: C % = 69.31; H % = 5.63.

Molecular weight: 326.

Identical according to NMR analysis.

Thin layer chromatographic test: see example 8.

Rf = 0.5.

Example 11

A mixture of 75 kg dimethyl-formamide, 100 kg (420 mole) of 7-hydroxy-isoflavone and 76 0 (550.7 mole) anhydrous potassium carbonate and 73 kg (598.3 mole) of isopropyl bromide are reacted at 75°-95° C. for 2 hours, and the mixture is maintained for 10 minutes at 100° C. To the reaction 45 kg of isopropanol and 350 kg of water are added under cooling. The crystal suspension is filtered and washed to neutral at 25° C. The wet product is crystallized in a 4.4-fold amount of anhydrous ethanol calculated to the dry substance content. The product is filtered with ethanol and dried at 60° C.

112.9 kg of 7-isopropoxy-isoflavone are obtained.

M.p.: 118°-119° C.

Active ingredient content: above 99.8% (HPLC), 7-ethoxy-isoflavone content: less than 0.1% and it does not contain contamination.

Yield: 96%.

We claim:

1. A process for the preparation of a pure compound of the Formula (I)

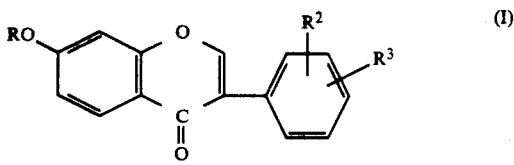

wherein
R is hydrogen or isopropyl; and
$R^2$ and $R^3$ are each hydrogen or $C_1$ to $C_2$ alkoxy; which comprises the steps of:
(a) cyclizing a compound of the Formula (III)

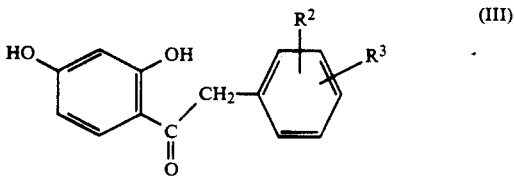

with a molar excess of ethyl orthoformate, at 70° to 100° C., in the presence of a catalytically effective amount of a base catalyst, in an organic solvent, wherein the ratio of the compound of the Formula (III) to the organic solvent is 0.3 to 2 by volume, to produce a reaction mixture which is a 20 to 70% by weight supersaturated solution of the compound of the Formula (I) where R is hydrogen;
(b) continuously precipitating the compound of the Formula (I) where R is hydrogen from the reaction mixture, under cooling;
(c) filtering the precipitate of the compound of the Formula (I) where R is hydrogen to obtain the compound in pure form, containing a contaminant compound of the Formula (VI)

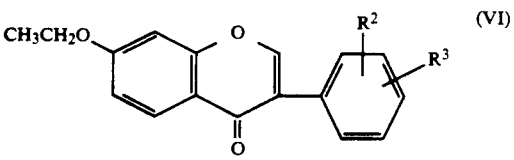

in an amount of only 0.1 to 0.5% by weight; and
(d) in the case where the compound of the Formula (I) having R as isopropyl is desired, alkylating the compound of the Formula (I) where R is hydrogen with an isopropyl halide alkylating agent in the presence of a potassium carbonate acid binding agent in acetone or dimethylformamide to obtain the compound of the Formula (I) where R is isopropyl and containing the contaminant compound of the Formula (VI) in an amount of only 0.1 to 0.5% by weight.

2. The process defined in claim 1 wherein according to step (a) the cyclization is carried out at 80° to 90° C. by using a heat treatment for 4 to 10 hours.

3. The process defined in claim 1 wherein according to step (a), ethanol, which is formed in the ring closing reaction, is retained in the reaction mixture.

4. The process defined in claim 1 wherein the base catalyst is a secondary amine.

5. The process defined in claim 1 wherein according to step (d) isopropyl bromide is added to the reaction mixture as the isopropyl halide.

6. The process defined in claim 1 wherein following step (c) a polar or apolar solvent is added to the reaction mixture to remove with dissolving a further amount of the contaminant compound of the Formula (VI) and the precipitated compound of the Formula (I) where R is hydrogen is filtered.

7. A process for the preparation of a pure compound of the Formula (I)

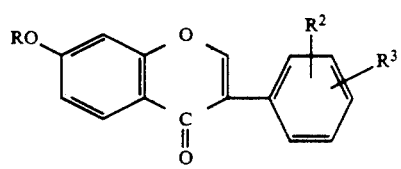

wherein
R is hydrogen or isopropyl; and
$R^2$ and $R^3$ are each hydrogen or $C_1$ to $C_2$ alkoxy which comprises the steps of:
(a) cyclizing a compound of the Formula (III)

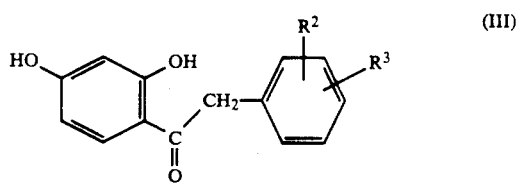

with a molar excess of ethyl orthoformate, at 70° to 100° C., in the presence of a catalytically effective amount of a base catalyst, in an organic solvent, wherein the ratio of the compound of the Formula (III) to the organic solvent is 0.3 to 2 by volume, to produce a reaction mixture which is a 20 to 70% by weight supersaturated solution of the compound of the Formula (I) where R is hydrogen;
(b) crystallizing the compound of the Formula (I) where R is hydrogen to form a crystallized suspension;
(c) distilling off a portion of the organic solvent employed during step (a);
(d) following step (c), adding a polar solvent to the reaction mixture;
(e) continuously precipitating the compound of the Formula (I) where R is hydrogen from the reaction mixture, under cooling;
(f) filtering the precipitate of the compound of the Formula (I) where R is hydrogen to obtain the compound in pure form, containing a contaminant compound of the Formula (VI)

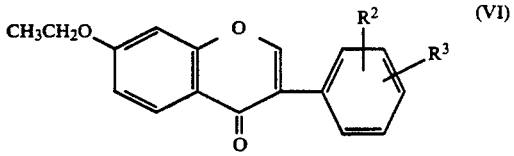

in an amount of only 0.1 to 0.5% by weight; and
(g) in the case where the compound of the Formula (I) having R as isopropyl is desired, alkylating the compound of the Formula (I) where R is hydrogen with an isopropyl halide alkylating agent in the presence of a potassium carbonate acid binding agent in acetone or dimethylformamide to obtain the compound of the Formula (I) where R is isopropyl and containing the contaminant compound of the Formula (VI) in an amount of only 0.1 to 0.5% by weight.

8. The process defined in claim 7 wherein according to step (a) the cyclization is carried out at 80° to 90° C. by using a heat treatment for 4 to 10 hours.

9. The process defined in claim 7 wherein according to step (a), ethanol, which is formed in the ring closing reaction, is retained in the reaction mixture.

10. The process defined in claim 7 wherein the base catalyst is a secondary amine.

11. The process defined in claim 7 wherein according to step (g) the isopropyl halide is isopropyl bromide.

12. A process for the preparation of a pure compound of the Formula (I)

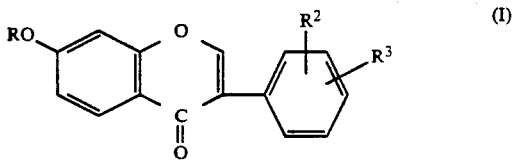

wherein
R is hydrogen or isopropyl; and
$R^2$ and $R^3$ are each hydrogen or $C_1$ to $C_2$ alkoxy; which comprises the steps of:
(a) cyclizing a compound of the Formula (III)

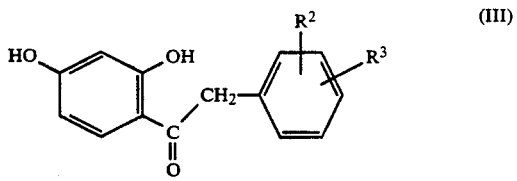

with a molar excess of ethyl orthoformate, at 70° to 100° C., in the presence of a catalytically effective amount of a base catalyst, in an organic solvent, wherein the ratio of the compound of the Formula (III) to the organic solvent is 0.3 to 2 by volume, to produce a reaction mixture which is a 20 to 70% by weight supersaturated solution of the compound of the Formula (I) where R is hydrogen;
(b) crystallizing the compound of the Formula (I) where R is hydrogen to form a crystallized suspension;
(c) following step (b), diluting the reaction mixture containing the crystallized suspension by adding thereto an apolar solvent;

(d) continuously precipitating the compound of the Formula (I) where R is hydrogen from the reaction mixture;
(e) filtering the precipitate of the compound of the Formula (I) where R is hydrogen to obtain the compound in pure form, containing a contaminant compound of the Formula (VI)

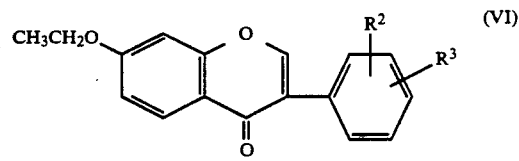

in an amount of only 0.1 to 0.5% by weight; and
(f) in the case where the compound of the Formula (I) having R as isopropyl is desired, alkylating the compound of the Formula (I) where R is hydrogen with an isopropyl halide alkylating agent in the presence of a potassium carbonate acid binding agent in acetone or dimethylformamide to obtain the compound of the Formula (I) where R is isopropyl and containing the contaminant compound of the Formula (VI) in an amount of only 0.1 to 0.5% by weight.

13. The process defined in claim 12 wherein according to step (a) the cyclization is carried out at 80° to 90° C. by using a heat treatment for 4 to 10 hours.

14. The process defined in claim 12 wherein according to step (a), ethanol, which is formed in the ring closing reaction, is retained in the reaction mixture.

15. The process defined in claim 12 wherein the base catalyst is a secondary amine.

16. The process defined in claim 12 wherein according to step (f) the isopropyl halide is isopropyl bromide.

17. The process defined in claim 12 wherein according to step (e) the precipitation of the compound of the Formula (I) is carried out while cooling the reaction mixture.

18. A process for the preparation of a pure compound of the Formula (I)

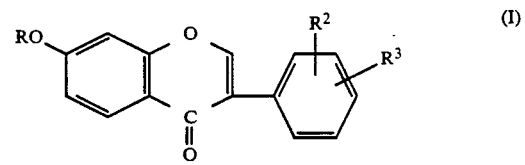

wherein
R is hydrogen or isopropyl; and
$R^2$ and $R^3$ are each hydrogen or $C_1$ to $C_2$ alkoxy; which comprises the steps of:
(a) cyclizing a compound of the Formula (III)

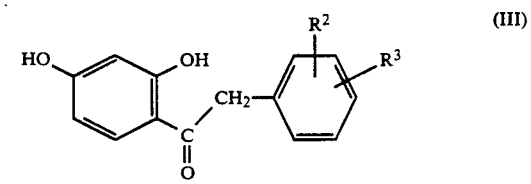

with a molar excess of ethyl orthoformate, at 70° to 100° C., in the presence of a catalytically effective amount of a base catalyst, in an organic solvent, wherein the ratio of the compound of the Formula (III) to the organic solvent is 0.3 to 2 by volume, to produce a reaction mixture which is a 20 to 70% by weight supersaturated solution of the compound of the Formula (I) where R is hydrogen;

(b) distilling off a portion of the organic solvent employed during step (a) to form the reaction mixture;

(c) adding to the reaction mixture an apolar solvent and an amount of anhydrous potassium carbonate that is the molar equivalent of the amount of the compound of the Formula (III) cyclized during step (a) under stirring at 60° to 65° C., followed by stirring at 0 to −5° C., to convert the compound of the Formula (I) where R is hydrogen to a crystallized salt of the Formula (V)

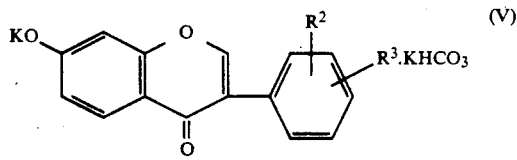

while leaving in solution a contaminant compound of the Formula (VI)

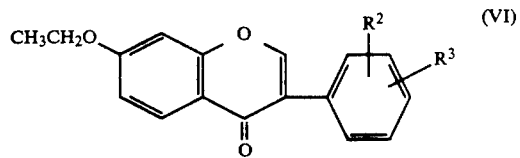

(d) separating the salt of the Formula (V) from the contaminant compound of the Formula (VI);

(e) dissolving the salt of the Formula (V) in a solution of methanol and water at 50° C. to 60° C. and adjusting the pH of the solution to 1 to form the pure compound of the Formula (I) where R is hydrogen containing only 0.1% by weight of the contaminant compound of the Formula (VI); and (f) in the case where the compound of the Formula (I) where R is isopropyl is desired, alkylating the compound of the Formula (I) where R is hydrogen with an isopropyl halide alkylating agent in the presence of a potassium carbonate acid binding agent in acetone or dimethylformamide to obtain the compound of the Formula (I) where R is isopropyl and containing the contaminant compound of the Formula (VI) in an amount of only 0.1% by weight.

19. The process defined in claim 18 wherein according to step (a) the cyclization is carried out at 80° to 90° C. by using a heat treatment for 4 to 10 hours.

20. The process defined in claim 18 wherein according to step (a), ethanol, which is formed in the ring closing reaction, is retained in the reaction mixture.

21. The process defined in claim 18 wherein the base catalyst is a secondary amine.

22. The process defined in claim 18 wherein according to step (c) the apolar solvent is toluene.

* * * * *